United States Patent
Elson et al.

(10) Patent No.: US 8,236,237 B2
(45) Date of Patent: Aug. 7, 2012

(54) METHOD AND APPARATUS FOR DESTRUCTION OF BIOLOGICAL AND CHEMICAL AGENTS

(75) Inventors: John Todd Elson, Albuquerque, NM (US); David E. Lane, Albuquerque, NM (US)

(73) Assignee: Fiore Industries, Inc., Albuquerque, NM (US)

( * ) Notice: Subject to any disclaimer, the term of this patent is extended or adjusted under 35 U.S.C. 154(b) by 1394 days.

(21) Appl. No.: 11/828,320

(22) Filed: Jul. 25, 2007

(65) Prior Publication Data

US 2012/0171074 A1    Jul. 5, 2012

Related U.S. Application Data

(60) Provisional application No. 60/833,005, filed on Jul. 25, 2006.

(51) Int. Cl.
*A61N 5/00* (2006.01)
*H05B 6/64* (2006.01)
*A61L 9/00* (2006.01)
*A62B 7/08* (2006.01)
*B01J 19/08* (2006.01)
*G01N 33/53* (2006.01)

(52) U.S. Cl. ............... 422/21; 422/1; 422/5; 422/121; 422/186; 422/900; 250/455.11; 250/492.1; 588/301; 588/310; 435/7.1; 435/292.1; 219/121.36; 219/678

(58) Field of Classification Search ............ 422/1, 5, 422/21, 121, 186, 900; 250/455.11, 492.1; 588/301, 310; 435/7.1, 292.1; 219/121.36, 219/678
See application file for complete search history.

(56) References Cited

U.S. PATENT DOCUMENTS

| | | | |
|---|---|---|---|
| 3,551,090 A * | 12/1970 | Robinson et al. | 422/21 |
| 5,019,344 A | 5/1991 | Kutner et al. | |
| 5,413,757 A | 5/1995 | Kutner et al. | |
| 6,039,921 A | 3/2000 | Boucher | |
| 6,303,316 B1 | 10/2001 | Kiel et al. | |
| 6,423,265 B1 | 7/2002 | Goldstein et al. | |
| 6,521,178 B1 | 2/2003 | Goldstein et al. | |
| 6,569,630 B1 | 5/2003 | Vivekananda et al. | |
| 6,806,439 B2 | 10/2004 | Uhm et al. | |
| 6,830,662 B2 | 12/2004 | Cha | |
| 7,198,750 B2 | 4/2007 | Czajkowski et al. | |
| 7,303,684 B2 | 12/2007 | Cha | |
| 2002/0197183 A1 | 12/2002 | Goldstein et al. | |
| 2003/0143629 A1 | 7/2003 | Holwitt | |
| 2003/0211005 A1 | 11/2003 | Sloan et al. | |
| 2004/0022668 A1 | 2/2004 | Kitchen | |
| 2005/0056785 A1 | 3/2005 | Chou et al. | |

OTHER PUBLICATIONS

Kiel, Johnathan L. et al., "Directed Killing of Anthrax Spores by Microwave-Induced Cavitation", *IEEE Transactions on Plasma Science* vol. 30, No. 4 Aug. 2002, 1482-1488.

* cited by examiner

*Primary Examiner* — Jill Warden
*Assistant Examiner* — Monzer Chorbaji
(74) *Attorney, Agent, or Firm* — Philip D. Askenazy; Peacock Myers, P.C.

(57) ABSTRACT

A device and method for inactivating infectious biological or chemical agents using microwave-activated diazoluminomelanin (DALM). The agents are typically vacuumed into a load cavity, which is at least partially filled with DALM. The load is irradiated with microwaves via a cylindrical waveguide disposed under the load cavity, thereby inactivating or destroying the agents. The system is preferably temperature controlled and operation is preferably automated.

26 Claims, 5 Drawing Sheets

METHOD AND APPARATUS FOR DESTRUCTION OF BIOLOGICAL AND CHEMICAL AGENTS

CROSS-REFERENCE TO RELATED APPLICATIONS

This application claims the benefit of the filing of U.S. Provisional Patent Application Ser. No. 60/833,005, entitled "Method and Apparatus to Inactivate Bacteria with Media Activated by Microwaves", filed on Jul. 25, 2006, and the specification thereof is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. FA8650-04-C-6466 awarded by the Air Force Research Laboratory.

BACKGROUND OF THE INVENTION

1. Field of the Invention (Technical Field)

The present invention is related to systems for destroying or inactivating biological entities and/or chemical compounds, including but not limited to biowarfare and chemical warfare agents, using microwave activated media.

2. Background Art

Note that the following discussion refers to a number of publications and references. Discussion of such publications herein is given for more complete background of the scientific principles and is not to be construed as an admission that such publications are prior art for patentability determination purposes.

Diazoluminomelanin (DALM), a water soluble polymer and organic semiconductor, is known to be activated as an anti-bacterial solution when exposed to microwave radiation. While microwaves alone can kill most bacteria or spores, such as anthrax spores, the presence of a microwave-activated chemical media can enhance that kill by increasing the kill ratio (the number of viable spores at the end of the exposure divided by the number of viable spores at the beginning of the exposure) or reducing the required time to achieve a desired kill ratio. See, for example U.S. Pat. Nos. 6,303,316 and 6,569,630, U.S. Patent Application Publication Nos. 2003/0143629 and 2003/0211005, and Kiel, et al., "Directed Killing of Anthrax Spores by Microwave-Induced Cavitation", IEEE Transactions on Plasma Science, vol. 30, no. 4, August 2002, pp. 1482-1488.

SUMMARY OF THE INVENTION

Disclosure of the Invention

The present invention is an apparatus for inactivating or destroying an agent, the apparatus comprising a collection system for collecting an agent, a microwave source, a cylindrical waveguide, a load chamber disposed on top of the waveguide, the load chamber for receiving the agent and receiving a solution comprising an organic semiconductor, and a temperature control system. The organic semiconductor preferably comprises diazoluminomelanin (DALM). The waveguide and the load chamber are preferably separated by a quarter-wave window, preferably comprised of a ceramic. The apparatus is preferably configured so that the solution absorbs a majority of microwave radiation. The collection system preferably comprises a vacuum and a filter, the filter comprising pores sufficiently small to trap the agent in the load chamber. The apparatus preferably further comprises one or more components selected from the group consisting of a refrigerated chamber for storing the solution; a solution precursor mixer; a photodetector for monitoring glow of the solution; an exhaust ducting system; an agent detector; a particle counter; and a solution level sensor. The apparatus of claim 1 preferably further comprises a battery and/or a portable cart for storing and transporting the apparatus. The microwave source is preferably a continuous wave source.

The present invention is also a method for inactivating or destroying an agent, the method comprising the steps of collecting the agent, depositing the agent in a load chamber, disposing an organic semiconductor in the load chamber, irradiating the agent and organic semiconductor with microwave radiation via a cylindrical waveguide disposed below the load chamber, activating the organic semiconductor, and controlling the temperature of the organic semiconductor during irradiation. The organic semiconductor preferably comprises diazoluminomelanin (DALM). The controlling step preferably comprises maintaining the temperature of the organic semiconductor below approximately 90° F. The microwave radiation is preferably continuous wave. The depositing step preferably comprises trapping the agent in the load chamber with a filter, and preferably contacting agent trapped in the filter with the organic semiconductor. The collecting step preferably comprises vacuuming up the agent.

The method preferably further comprises on or more of the following steps: coupling a majority of the microwave radiation to the organic semiconductor, monitoring a glow of the organic semiconductor during the irradiation step, portably storing refrigerated precursors to the organic semiconductor, monitoring particle sizes during the collecting step, transporting the load chamber and waveguide to a contaminated location, decontaminating a surface or area contaminated with the agent, automatically mixing the precursors within a short time prior to the disposing step, testing an activity of the organic semiconductor before the irradiating step, determining the existence of any active agent after the irradiating step, and/or measuring a level of the organic semiconductor in the load chamber.

An object of the present invention is to provide a portable system for removing and destroying harmful biological or chemical agents, including but not limited to anthrax.

An advantage of the present invention is that it can be battery powered and is sufficiently portable to be moved throughout a building, including through standard doorways and hallways.

Another advantage of the present invention is that it can remove agents from materials which are commonly found in an office to which anthrax spores could be exposed, including but not limited to carpet, plastic, metals, glass, paper, or wood.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

DESCRIPTION OF THE PREFERRED EMBODIMENTS

Best Modes for Carrying Out the Invention

As used throughout the specification and claims, "agent" means any biological entity such as any biowarfare agent, infectious disease causing vector, bacteria, virus, parasite, spore, including but not limited to anthrax spores or *Bacillus Thuringiensis* spores, or any chemical compound, chemical warfare agent, poison gas, nerve gas, toxin, and the like.

It has been discovered that there are two reactions that DALM undergoes when irradiated by microwaves: a singlet energy transition that forms a blue glow, and breakdown via free radical formation from a triplet energy transition. It has further been discovered in the present invention that free radical formation is responsible for most of the anti-agent activity observed. Temperature determines which reaction is dominant and how long the reactions last. The singlet reaction is dominant at higher temperatures; during irradiation DALM can get hot enough to boil. In addition, boiling DALM can shoot agents into the air. Therefore it is important to enclose the system and to control the temperature of the DALM to ensure that free radical formation is the primary reaction during irradiation. However, the blue glow can be used to confirm that activated DALM is still present.

Figure 1:
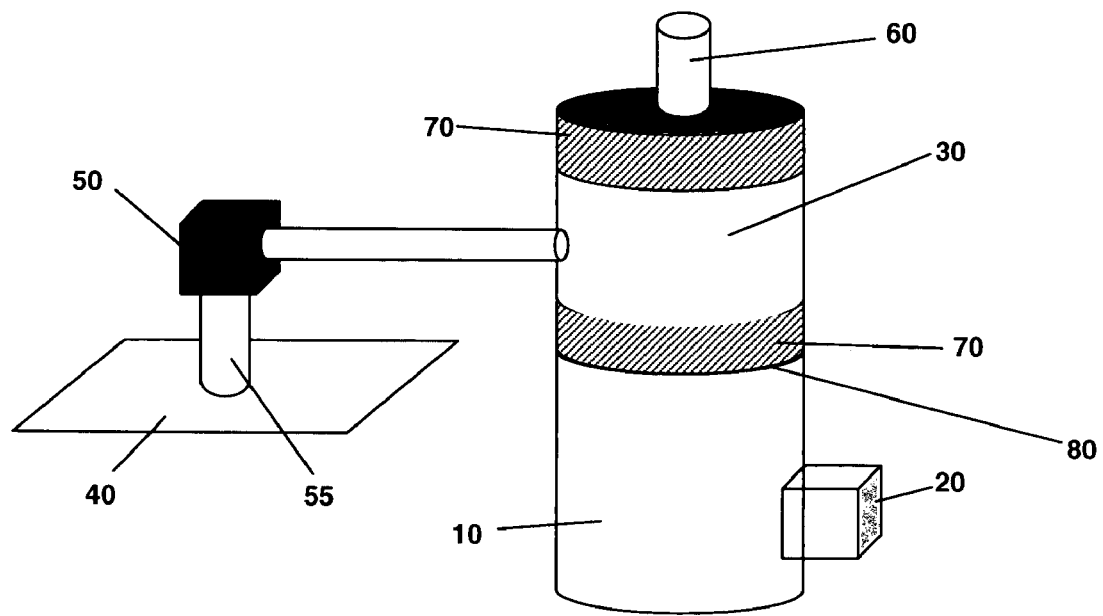
FIG. 1 is a schematic of an embodiment of the present invention.
Figure 2:
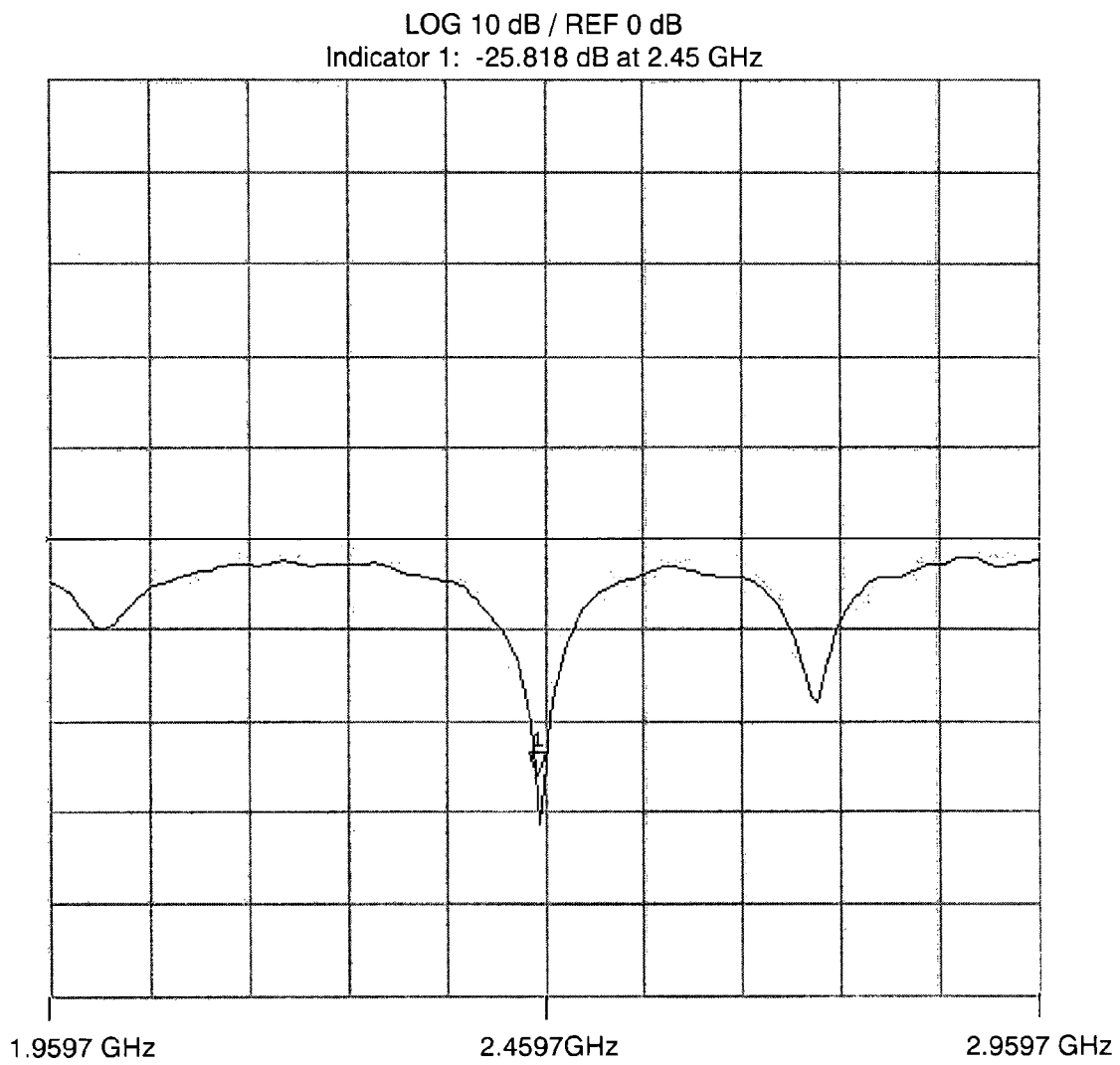
FIG. 2 shows enhanced absorption of microwave energy by the DALM at the microwave frequency.

It has been discovered that activated DALM works best in closed systems. As shown in the schematic of FIG. 1, the system preferably comprises cylindrical waveguide 10 which delivers the power from microwave source 20 to load section 30, which is configured to contain an absorbing load which preferably comprises DALM or another similar medium. Waveguide 10 is preferably circular in cross-section for more even mixing of the DALM solution, but may alternatively be rectangular or comprise any other shape. Microwave source 20 preferably comprises a continuous wave 2.45 GHz source, although any frequency from 1-10 GHz may be used. The output of the microwave source, which preferably comprises a magnetron, is preferably stabilized by controlling the temperature of the source. Proper tuning of the system coupled approximately 99% of the magnetron power to the DALM load, as shown by the strong absorption of DALM at the microwave frequency in FIG. 2. In addition, the load is preferably over five microwave skin depths deep so that almost all microwave power is absorbed by the DALM solution. The containment of microwaves in waveguide 10 eliminates exposure to humans and sensitive equipment.

Preferably quarter-wave window 80, preferably comprising a ceramic, separates the waveguide and load section 30 to reduce or eliminate reflection of microwaves back to the source. If settling of the solution in load section 30 causes the electromagnetic properties to change significantly near the window, causing a microwave reflection, the load can be periodically stirred, such as with an impeller or magnetic stirrer, to maintain continuity of the solution. However, load section 30 is preferably located at the top of the system, above the microwave source, in part to eliminate air bubbles which form an air gap by window 80 that causes unwanted microwave reflections. Thus, any settling of agents would be on window 80 where the fields are strongest. In addition, since the solution at the bottom of load section 30 near window 80 heats up first, convection in the solution occurs, thereby mixing the solution. Thus it is preferable that no mechanical stirring is used. Further, in some configurations mechanical stirring may interfere with activation of the DALM.

Agents are preferably transferred to load section 30 either by direct placement or vacuum. Small objects, comprising agents, that are small enough to fit within the load may be decontaminated directly, while agents on surface 40 of large objects, such as floors or tables, or are suspended in the air, are preferably removed via hose 55 and disposed in load 30 using vacuum system 50, preferably comprising appropriately-sized filters to prevent entrance of large particulates and/or trap the agents inside load section 30 so they cannot exit the system via vacuum outlet 60.

Figure 3:
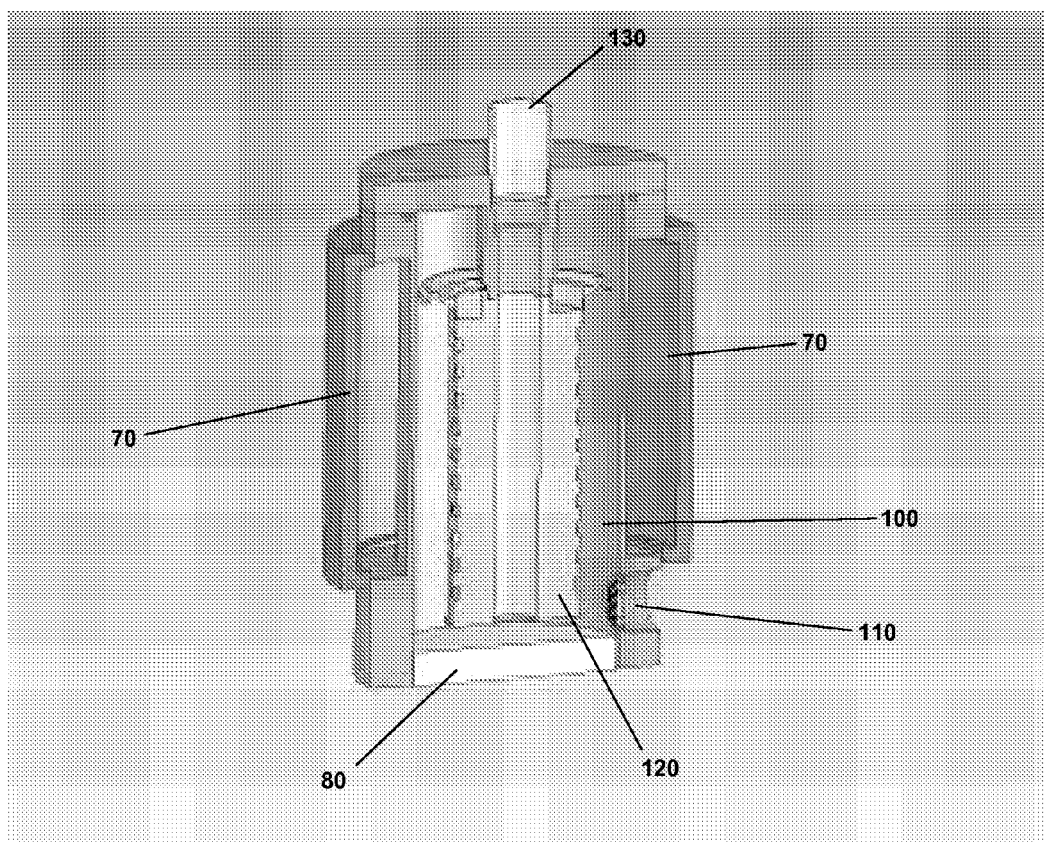
FIG. 3 is a cross section of the load section of the present invention.

FIG. 3 is a detailed cross section of load section 30. Agents are introduced into load section 30 via vacuum inlet 110 and are trapped in chamber 100 by submicron filter 120. It is anticipated that vacuuming of contaminated surfaces will last for approximately thirty minutes, although this time is limited only by the amount of battery power available. Filtered exhaust air exits load section 30 via vacuum outlet 130. Vacuum inlet 110 is then preferably closed. The DALM solution, which is preferably premixed and preferably stored in a storage chamber, is preferably then introduced into chamber 100. Alternatively, the DALM solution may already be present in chamber 100. The DALM solution and the incorporated agents are then irradiated by microwaves via quarter wave window 80, typically for approximately thirty minutes, thereby inactivating or destroying the agents.

Weapons grade anthrax powder is typically 1 to 5 microns in size. In order to trap all agent particles, it is preferable that a filter with pores less than one micron is employed. Tradeoff of pore size, filter size, and flow rate must be made. The present system preferably uses 0.4 micron filters, which have sufficient flow rate and a reasonable size of 3 to 6 inches in length for a 3 inch diameter cartridge. Because the filter is in contact with the activated DALM solution, agents trapped in the filter matrix are also inactivated or destroyed.

Because DALM has a limited shelf life and is temperature sensitive, storage requires refrigeration and mixing the final compounds right before use. Thus the present invention optionally includes a refrigerated chamber for storing DALM and/or its precursors, and a mixer for mixing the constituent compounds when desired. The ratio of compounds greatly effects the activation duration of DALM. However, an indicator that activated DALM is present is detecting it glowing in the presence of microwaves. Thus the present system preferably comprises a detector, such as a UV fiber-optic sensor or photodiode, used to monitor DALM glow and therefore activity. The main peak seen on activated DALM was near 480 nm (visible blue). In addition, the present system may optionally comprise a pre-test process, for example comprising automatically testing a sample of the mixed DALM in a test chamber, to ensure that the DALM has been mixed properly and will be effective. The amount of DALM to number of spores has already been shown to be significant. It is possible to not have enough DALM in solution to kill all the spores present.

The system also preferably comprises a temperature management system to maintain appropriate temperatures of various components. Such system may use any means known in the art, including but not limited to Peltier cells. Preferably one or more cooling jackets 70, containing circulating chilled water, at least partially surround load section 30, and optionally microwave source 20, thereby controlling the temperature of the load within load section 30. The system optionally comprises an inlet and an outlet port so that the DALM solution can be cooled and re-circulated. Some components of the system are forced air cooled (typically via fans); combined with the exhaust from the vacuum, a lot of air movement may be produced. Thus the system optionally comprises a ducting system for transporting such exhaust air external to the contaminated area, so the agents in the area are not further dispersed.

The system preferably comprises one or more batteries to enable portable usage. The batteries may be any known in the art, but preferably comprise rechargeable lithium polymer batteries. As an example, for a 1 kW microwave source, it is preferable to employ enough batteries to provide approximately 3000 W of power for one hour. Alternatively the system may be operated by standard 120 VAC power, especially useful for systems designed for use inside a building.

Figure 4:
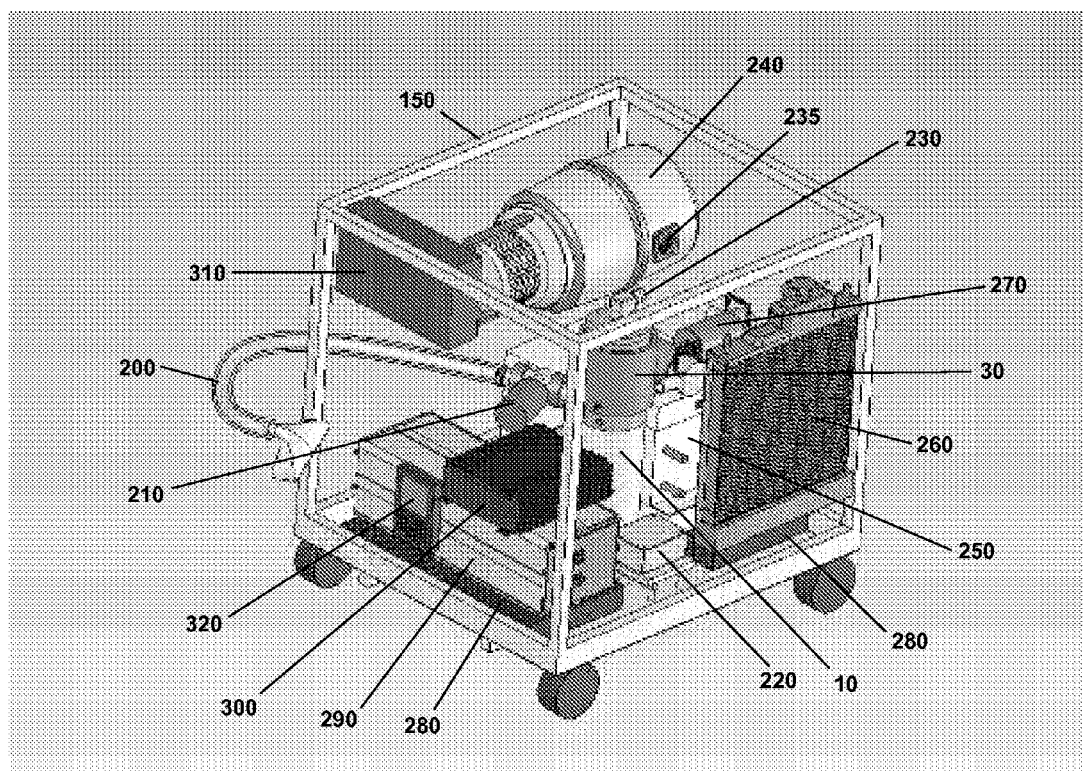
FIG. 4 shows a portable prototype embodiment of the present invention.

FIG. 4 shows an embodiment of the system of the present invention attached to portable cart 150. Plumbing, wiring, and shelving are not shown. Pictured are vacuum hose 200, solenoid 210 for closing off the vacuum inlet, power supply 220 for the microwave magnetron (not visible), cylindrical waveguide 10, load section 30, vacuum exhaust outlet 230, which is connected to intake 235 of vacuum 240 via a hose (not shown), water chiller 250, which is connected to radiator 260, water pump 270, battery packs 280, and power inverter 290 for providing power to AC operated components.

Operation of the system is preferably automated and controlled by computer 300 via relay/sensor box 310. Operation is monitored via display 320, which can optionally be mounted on the top surface of cart 150 (not shown). Alternatively, a computer monitor connected to computer 300 may be mounted on cart 150, or computer 300 may transmit a wireless or other signal to a remote monitoring location.

Figure 5:
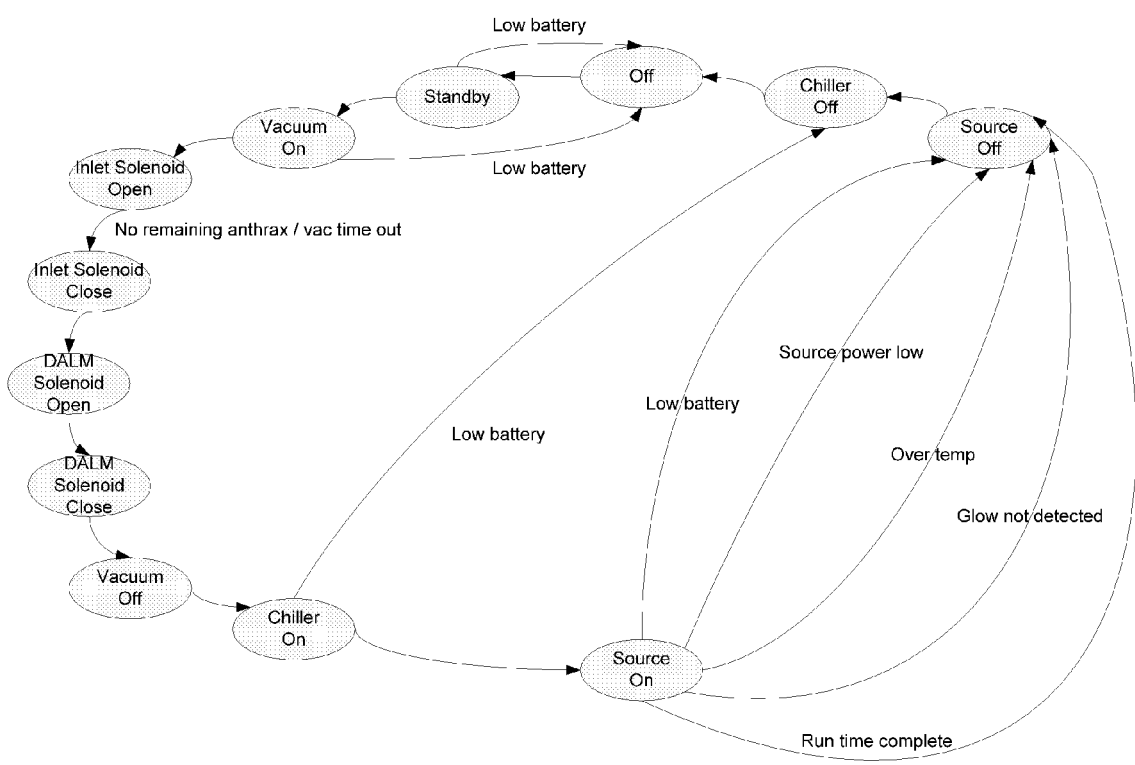
FIG. 5 is an example state diagram for automated operation of the present invention.

A state diagram of one embodiment of the automated process of the present invention is displayed in FIG. 5. The preferable use of sensors and feedback loops enable the operator to optimize and/or automate control over operation over the system. A sensor, such as an anthrax detector, for detecting whether or not all agents have been vacuumed from a contaminated area is preferably installed prior to the vacuum inlet. Alternatively, a particle counter can be used; after no further particles in the 1 to 5 micron range (if anthrax is the agent) are detected, it can be safely assumed that all anthrax in the area has been vacuumed into the system. Another sensor, such as an anthrax detector disposed in load section 30, may be used after operation of the device to ensure that the used DALM solution does not contain any active agents, thus permitting safe disposal of the solution. In addition to those sensors discussed above, other sensors that may be used include:

digital temperature probes for measuring the DALM load, the cooling fluid, and the magnetron;

a microwave power probe for measuring microwave energy in the DALM solution;

a voltage probe for measuring battery system output; and a water level sensor for measuring the fluid level in the load chamber.

Example

During prototype development it was determined that for a 300 ml volume the kill ratio for *Bacillus Thuringiensis* spores was $10^3$ for 10 minutes; all of the tests with 600 and 900 ml volumes indicated zero colony forming units after exposure. Liquid cultures of *Bacillus anthracis* (anthrax-Sterne strain) at a concentration of $8 \times 10^6$ CFU/ml were then tested in sample solutions:

1. $B.a.$+Luminol*+$H_2O_2$(0.3%)+DALM(*Saturated solution of Luminol with $NaHCO_3$)

Following microwave exposure, *B. a.* spores were extracted from the waveguide, serially diluted and plated onto Tryptic Soy Agar (TSA) plates to determine concentration of viable spores by colony counts. Amount killed was calculated by comparing a non-microwaved sample with each solution to the microwaved samples.

Variation 1: 900 ml sample solutions were microwaved at approximately 1 kW power for exposure times of 10 minutes and 20 minutes. Duplicate testing was conducted at this time in order to confirm results.

Variation 2: A wide mouth port was placed upon the waveguide apparatus in order to reduce solution loss due to the $H_2O_2$ chemical reaction. Solutions were microwaved at exposure times of 10 and 20 minutes with minimal solution loss.

Variation 3: The waveguide was modified to include a cooling apparatus which helped to control temperature, reducing the amount of solution loss.

Data analysis based on colony counts showed significant decreases when the solution was kept below approximately 90° F. in surviving spores from all of the experiments where spores were microwaved along with the solutions for 10 minutes and 20 minutes. Thus DALM/microwave treatments were effective when exposed at 900 ml volumes within the waveguide. Test results found at 10 minutes of exposure time were 10 cfu/ml and <10 cfu/ml at 20 minutes of exposure time. This confirms that the kill seen using the BT spores will also work with anthrax.

Although the invention has been described in detail with particular reference to these examples and embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. An apparatus for inactivating or destroying an agent, the apparatus comprising:
   a collection system for collecting an agent, said collection system comprising a vacuum and a filter;
   a microwave source;
   a cylindrical waveguide;
   a load chamber disposed on top of said waveguide, said load chamber for receiving said agent and receiving a solution comprising an organic semiconductor; and
   a temperature control system;
   wherein said filter comprises pores sufficiently small to trap the agent in said load chamber.

2. The apparatus of claim 1 wherein said organic semiconductor comprises diazoluminomelanin (DALM).

3. The apparatus of claim 1 wherein said waveguide and said load chamber are separated by a quarter-wave window.

4. The apparatus of claim 3 wherein said window is comprised of a ceramic.

5. The apparatus of claim 3 configured so that said solution absorbs a majority of microwave radiation.

6. The apparatus of claim 1 further comprising one or more components selected from the group consisting of a refrigerated chamber for storing said solution; a solution precursor mixer; a photodetector for monitoring glow of the solution; an exhaust ducting system; an agent detector; a particle counter; and a solution level sensor.

7. The apparatus of claim 1 further comprising a portable cart for storing and transporting said apparatus.

8. The apparatus of claim 1 wherein the microwave source is a continuous wave source.

9. The apparatus of claim 1 further comprising a battery.

10. A method for inactivating or destroying an agent, the method comprising the steps of:
    collecting the agent;
    depositing the agent in a load chamber;
    disposing an organic semiconductor in the load chamber;
    irradiating the agent and organic semiconductor with microwave radiation via a cylindrical waveguide disposed below the load chamber;
    activating the organic semiconductor; and
    controlling the temperature of the organic semiconductor during irradiation.

11. The method of claim 10 wherein the organic semiconductor comprises diazoluminomelanin (DALM).

12. The method of claim 10 further comprising the step of coupling a majority of the microwave radiation to the organic semiconductor.

13. The method of claim 10 further comprising the step of monitoring a glow of the organic semiconductor during the irradiation step.

14. The method of claim 10 wherein the controlling step comprising maintaining the temperature of the organic semiconductor below approximately 90° F.

15. The method of claim 10 wherein the depositing step comprises trapping the agent in the load chamber with a filter.

16. The method of claim 10 further comprising the step of contacting agent trapped in the filter with the organic semiconductor.

17. The method of claim 10 further comprising the step of monitoring particle sizes during the collecting step.

18. The method of claim 10 further comprising the step of transporting the load chamber and waveguide to a contaminated location.

19. The method of claim 18 further comprising the step of decontaminating a surface or area contaminated with the agent.

20. The method of claim 10 wherein the collecting step comprises vacuuming up the agent.

21. The method of claim 10 further comprising the step of portably storing refrigerated precursors to the organic semiconductor.

22. The method of claim 21 further comprising the step of automatically mixing the precursors within a short time prior to the disposing step.

23. The method of claim 10 further comprising the step of testing an activity of the organic semiconductor before the irradiating step.

24. The method of claim 10 further comprising the step of determining the existence of any active agent after the irradiating step.

25. The method of claim 10 further comprising the step of measuring a level of the organic semiconductor in the load chamber.

26. The method of claim 10 wherein the microwave radiation is continuous wave.

* * * * *